United States Patent [19]

Martin et al.

[11] 4,351,961
[45] Sep. 28, 1982

[54] 2-(2′,2′-DICHLORO-3′,3′,3′-TRIFLUORO-PROPYL)- AND 2-(2′,2′,3′-TRICHLORO-3′,3′-DIFLUORO-PROPYL)-4-CHLOROCYCLOBUTAN-1-ONES

[75] Inventors: Pierre Martin, Rheinfelden; Eginhard Steiner, Füllinsdorf; Daniel Bellus, Riehen, all of Switzerland

[73] Assignee: Ciba-Geigy Corporation, Ardsley, N.Y.

[21] Appl. No.: 210,892

[22] Filed: Nov. 28, 1980

[30] Foreign Application Priority Data

Dec. 7, 1979 [CH] Switzerland ............... 10869/79

[51] Int. Cl.³ .......................................... C07C 49/457
[52] U.S. Cl. .................................................. 568/381
[58] Field of Search ........................................ 568/381

[56] References Cited

U.S. PATENT DOCUMENTS

| | | | |
|---|---|---|---|
| 3,140,298 | 7/1964 | England | 568/381 |
| 4,234,517 | 11/1980 | Greuter et al. | 568/381 |
| 4,242,278 | 12/1980 | Martin et al. | 568/381 |

FOREIGN PATENT DOCUMENTS

| | | | |
|---|---|---|---|
| 2813337 | 10/1978 | Fed. Rep. of Germany | 568/381 |
| 2813338 | 10/1978 | Fed. Rep. of Germany | 568/381 |
| 2842601 | 3/1979 | Fed. Rep. of Germany | 568/381 |
| 1584260 | 2/1981 | United Kingdom | 568/381 |

*Primary Examiner*—Natalie Trousof
*Assistant Examiner*—James H. Reamer
*Attorney, Agent, or Firm*—Frederick H. Rabin

[57] ABSTRACT

Compounds of the formula I

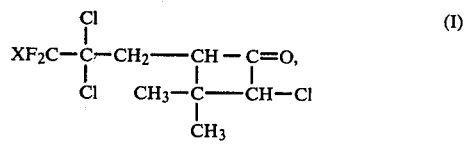

wherein X is chlorine or fluorine, are suitable for producing 2,2-dimethyl-3-(2′-chloro-3′,3′,3′-trifluoroprop-1′-en-1′-yl)- and 2,2-dimethyl-3-(2′,3′-dichloro-3′,3′-difluoroprop-1′-en-1′-yl)-cyclopropanecarboxylic acids and insecticidally effective esters thereof (pyrethroids). The cyclobutanones (I) can be produced by the addition reaction of 2,4,4,5-tetrachloro-5,5-difluoro- or 2,4,4-trichloro-5,5,5-trifluoropentane-1-carboxylic acid chloride with isobutylene, and rearrangement of the resulting 2-chloro-2-(2′,2′,3′-trichloro-3′,3′-difluoropropyl)- or 2-chloro-2-(2′,2′-dichloro-3′,3′,3′-trifluoropropyl)-3,3-dimethylcyclobutan-1-one in the presence of catalysts.

2 Claims, No Drawings

2-(2',2'-DICHLORO-3',3',3'-TRIFLUOROPROPYL)- AND 2-(2',2',3'-TRICHLORO-3',3'-DIFLUOROPROPYL)-4-CHLOROCYCLOBUTAN-1-ONES

The invention relates to novel 2-(2',2'-dichloro-3',3',3'-trifluoropropyl)- and 2-(2',2',3'-trichloro-3',3'-difluoropropyl)-4-chlorocyclobutan-1-ones, to a process for producing them, and to the novel intermediates usable for producing them.

It is known from the German Offenlegungsschriften Nos. 2,813,337 and 2,842,601 that 2-(2',2',2'-trihaloethyl)-4-halocyclobutan-1-ones can be produced by reaction of 2,4,4,4-tetrahalobutyric acid chlorides with olefins, such as isobutylene, and rearrangement of the resulting 2-(2',2',2'-trihaloethyl)-2-halocyclobutan-1-ones in the presence of catalysts.

It has now been found that novel 4-chlorocyclobutan-1-ones of the formula I

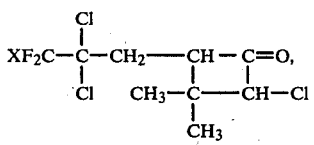

wherein X is chlorine or fluorine, can be produced in a simple manner, with use of readily accessible starting products, by reacting a compound of the formula II

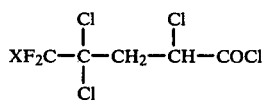

in which X has the meaning given under the formula I, in the presence of an organic base, with isobutylene to give a 2-(2',2'-dichloro-3',3',3'-trifluoropropyl)- or 2-(2',2',3'-trichloro-3',3'-difluoropropyl)-2-chlorocyclobutan-1-one of the formula III

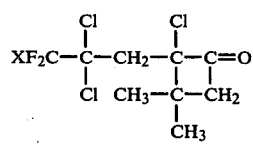

wherein X has the meaning defined under the formula I, and subsequently rearranging this compound, in the presence of a catalyst, into a compound of the formula I.

The cyclobutanones of the formula III and the 2,4,4,5-tetrachloro-5,5-difluoro- and 2,4,4-trichloro-5,5,5-trifluoropentane-1-carboxylic acid chlorides of the formula II are novel compounds. The last-mentioned can be produced, in a manner known per se, by adding by reaction a compound of the formula IV

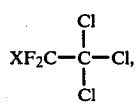

in which X has the meaning given under the formula I, to a compound of the formula V

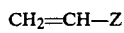

$$CH_2=CH-Z \quad (V)$$

in which Z is chlorocarbonyl, carboxyl, alkoxycarbonyl having 1-4 C atoms in the alkyl group or cyano; and converting resulting compounds of the formula VI

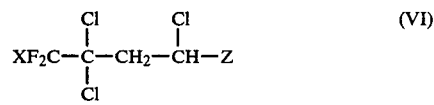

in which X has the meaning defined under the formula I, and Z is carboxyl, alkoxycarbonyl having 1-4 C atoms in the alkyl moiety, or cyano, into compounds of the formula VI wherein Z is chlorocarbonyl. The compounds of the formula VI are novel and likewise form subject matter of the present invention.

In the addition reaction of a compound of the formula IV with an acrylic acid derivative of the formula V, the compound of the formula IV can be used in a stoichiometric amount. Preferably however an excess of the compound of the formula IV is used, for example an approximately 0.5- to 2-fold molar excess, the compound of the formula IV being also able to serve as solvent.

The addition reaction of a compound of the formula IV with a compound of the formula V is performed in the presence of a catalyst. Suitable catalysts are metals of the main group VIII and of the subgroups VIa, VIIa and Ib of the periodic system, in elementary form or in the form of compounds, particularly in the form of salts or complexes, especially catalysts of the type described in the German Offenlegungsschrift No. 2,813,337. Iron-(II) and iron(III) salts and complexes as well as iron powder are preferably used, particularly however copper powder, copper(I) and copper(II) salts and complexes, such as Cu(I) chloride, Cu(II) chloride, Cu(I) bromide, Cu(II) bromide, Cu(I) iodide, Cu(II) acetylacetonate, Cu(II) benzoylacetonate, Cu(II) sulfate, Cu(II) nitrate and Cu(I) cyanide. More particularly preferred are copper powder, copper(I) and copper(II) chloride or bromide, as well as mixtures thereof.

The stated catalysts are in general used in amounts of about 0.01 to 10 mol %, preferably 0.1 to 5 mol %, relative to the compound of the formula IV.

The addition reactions are performed in an organic solvent. Suitable organic solvents are those in which the catalysts are sufficiently soluble, or which can form with the catalysts complexes, which however are inert to the starting compounds, for example solvents of the type described in the aforementioned German Offenlegungsschrift No. 2,813,337. Preferred solvents are alkyl nitriles having 2–5 C atoms and 3-alkoxypropionitriles having 1 or 2 C atoms in the alkoxy moiety, especially acetonitrile and 3-methoxypropionitrile. The reaction temperatures are generally between about 60° and 200° C., particularly between about 80° and 170° C.

When acrylic acid chloride is used as compound of the formula V, there is obtained directly in pure form the desired compound of the formula VI wherein Z is chlorocarbonyl. In the case where acrylic acid is used as the compound of the formula V, the free 2,4,4,5-tetrachloro-5,5-difluoro- or 2,4,4-trichloro-5,5,5-trifluoropentane-1-carboxylic acid obtained can subsequently be readily converted in a manner known per se, by reaction with inorganic acid chlorides, such as phosphorus trichloride, phosphorus pentachloride, phosphorus oxychloride, phosgene, thionyl chloride or oxalyl chloride, into the corresponding acid chloride. The esters or nitriles of the formula VI (Z=alkoxycarbonyl or cyano), which are obtained with use of compounds of the formula V in which Z is alkoxycarbonyl or cyano, are firstly hydrolysed in the presence of strong acids, such as concentrated hydrochloric acid, to the corresponding free acid, which is then converted in the aforementioned manner into the acid chloride.

The reaction of the compounds of the formula II with isobutylene to obtain the cyclobutanones of the formula III and also the rearrangement thereof to compounds of the formula I are performed substantially under reaction conditions analogous to those described in the German Offenlegungsschrift No. 2,813,337.

The reaction of the acid chlorides of the formula II with isobutylene is advantageously performed in the presence of an inert organic solvent. Particularly suitable solvents are aliphatic, cycloaliphatic and aromatic hydrocarbons, especially alkanes having 5 to 8 C atoms, benzene and toluene and in particular n-hexane and cyclohexane. Excess isobutylene can also serve as solvent. Suitable organic bases for the above reaction are for example tertiary amines, especially trialkylamines having 1-4 C atoms in each of the alkyl moieties, cyclic amines, bicyclic amidines and bicyclic diamines. Particularly suitable organic bases are trialkylamines having 1-4 C atoms in each of the alkyl moieties, especially triethylamine, and pyridine.

The organic base is used in at least the equimolar amount or in a slight excess relative to the acid chloride of the formula II. The isobutylene is likewise used in at least the equimolar amount relative to the acid chloride of the formula II. It is however in general advantageous to use an excess of isobutylene, the isobutylene, as already mentioned, being able to also serve as solvent. The reaction temperatures are in general between 0° and 200° C., preferably between 20° and 160° C.

Acids, bases or quaternary ammonium, phosphonium or sulfonium halides of the type mentioned in the German Offenlegungsschrift No. 2,813,337 can be used as catalysts for the rearrangement of the cyclobutanones of the formula III into compounds of the formula I. Suitable basic catalysts are in particular primary, secondary and tertiary amines and trialkylphosphines. The catalysts used are above all organic and inorganic protonic acids, especially hydrohalic acids. Finally, it is possible to use as catalysts also salts of protonic acids with organic bases containing ammonia or nitrogen, such as trialkylaminohydrochlorides and -bromides having 1-8 C atoms in each of the alkyl groups. Preferred catalysts are trialkylamines having 1-8 C atoms in each alkyl group, hydrohalic acids and tetraalkylammonium halides having 1-18 C atoms in each of the alkyl groups. The amount of catalyst used can vary within wide limits. It suffices in some cases when the catalyst is present in traces. In general however the catalyst is preferably used in an amount of about 0.1 to 15 percent by weight, relative to the compound of the formula III. The rearrangement reaction can be performed both in the melt and in an inert organic solvent. The reaction temperature for rearrangement in the melt is generally between about 60° and 150° C., especially between about 80° and 130° C. Suitable catalysts for the rearrangement reaction in the melt are in particular organic bases, especially trialkylamines having 1-8 C atoms in each of the alkyl moieties, and more particularly tetraalkylammonium halides, above all tetraalkylammonium chlorides, bromides and iodides, having 1-18 C atoms in each alkyl moiety.

Suitable organic solvents are for example optionally nitrated or halogenated aliphatic, cycloaliphatic or aromatic hydrocarbons, aliphatic alcohols having up to 6 C atoms, aliphatic diols, ethylene glycol mono- and -dialkyl ethers and diethylene glycol mono- and dialkyl ethers having 1-4 C atoms in each of the alkyl moieties, cyclic amides, amides of carbonic acid, amides of phosphorous acid, of phosphoric acid, of phenylphosphonic acid or of aliphatic phosphonic acids having 1-4 C atoms in the acid moiety, amides of sulfuric acid, of aliphatic or aromatic sulfonic acids, organic sulfones and sulfoxides, aliphatic and aromatic nitriles, 3-alkoxy-propionitriles having 1 or 2 C atoms in the alkoxy moiety, aliphatic ketones preferably having all together 3–8 C atoms, alkyl and alkoxyalkyl esters of aliphatic monocarboxylic acids having all together 2-6 C atoms, cyclic ethers, dialkyl ethers having 1-4 C atoms in each of the alkyl moieties and N,N-dialkylamides of aliphatic monocarboxylic acids having 1-3 C atoms in the acid moiety.

For the rearrangement in the presence of an acid catalyst, for example an organic or inorganic protonic acid, such as a hydrohalic acid, there are advantageously used polar solvents, particularly lower alcohols, such as methanol, ethanol or butanols, N,N-dialkylamides of aliphatic monocarboxylic acids having 1-3 C atoms in the acid moiety, especially N,N-dimethylformamide, or dialkylsulfoxides, such as dimethylsulfoxide.

In aprotic, strongly polar solvents, such as in the aforementioned N,N-disubstituted amides of aliphatic monocarboxylic acids, cyclic amides, amides of carbonic acid, amides of phosphorous acid, of phosphoric acid, of phenylphosphonic acid or of aliphatic phosphonic acids, amides of sulfuric acid or of aliphatic or aromatic sulfonic acids, as well as of dialkylsulfoxides, such as dimethylsulfoxide, the reaction proceeds also without addition of a base or acid. In these cases, the solvent acts as catalyst. In general however where the rearrangement reaction is performed in the presence of an inert organic solvent a catalyst is added, preferably an organic base having a $pK_a$ value of above 9, particularly trialkylamines having 1-8 C atoms in each of the alkyl moieties, such as triethylamine, tri-n-butylamine and tri-n-octylamine; also hydrohalic acids, especially HCl and HBr, as well as tetraalkylammonium halides, in particular tetraalkylammonium chlorides, bromides and iodides, having 1-18 C atoms in each of the alkyl moieties.

Particularly preferred solvents are aliphatic alcohols having 1-4 C atoms, toluene, xylenes, chlorobenzene, dioxane, acetonitrile, 3-methoxypropionitrile, ethylene glycol diethyl ether and diisopropyl ketone. The reaction temperatures for the rearrangement in the presence of an inert organic solvent are in general between about 0° and 150° C., preferably between about 80° and 130° C.

There are obtained by the present invention in a simple manner and in good yield, commencing with readily accessible starting materials, novel 2-(2',2'-dichloro-3',3',3'-trifluoropropyl)- and 2-(2',2',3'-trichloro-3',3'-difluoropropyl)-4-chlorocyclobutan-1-ones each substituted in the 3-position, which are suitable for producing 2-(2'-chloro-3',3',3'-trifluoroprop-1'-en-1'-yl)- and 2-(2',3'-dichloro-3',3'-difluoroprop-1'-en-1'-yl)-cyclopropanecarboxylic acids, -carboxylic acid halides and insecticidally effective esters thereof, each substituted in the 3-position. Such cyclopropanecarboxylic acids, cyclopropanecarboxylic acid halides and insecticidally effective esters thereof can be described for example by the following formula VII

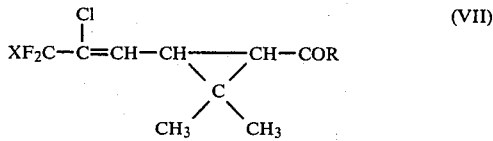

in which X has the meaning defined under the formula I, and R is —OH, halogen, particularly chlorine, alkoxy having 1–6 C atoms, or a group of the formula VIII or IX

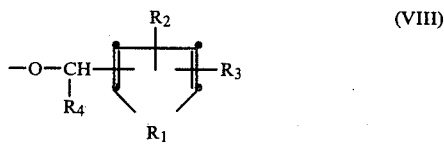

or

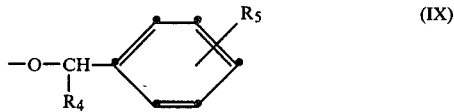

wherein $R_1$ is —S— and particularly —O—, $R_2$ is hydrogen or alkyl, especially methyl, and is bound in the 2- or 3-position to the heterocyclic ring, $R_3$ is benzyl or phenoxy, and is bound in the 4- or 5-position to the heterocyclic ring, $R_4$ is hydrogen, cyano or ethynyl, and $R_5$ is 3-phenyl, 3-phenoxy or 3-benzyl.

The cyclopropanecarboxylic acid derivatives of the formula VII in which R is a group of the formula VIII or IX are suitable for combating insects and similar pests, such as Acarina. The properties, fields of application and forms of application of these active substances (pyrethroids) are described for example in the German Offenlegungsschriften Nos. 2,802,962 and 2,907,609, and also in the EP Publication No. 0003336.

The conversion of compounds of the formula I into compounds of the formula VII is performed in a manner known per se by heating in the presence of suitable bases. Suitable bases are for example hydroxides of alkali metals and alkaline-earth metals, such as sodium hydroxide, potassium hydroxide, calcium hydroxide and barium hydroxide. It is also possible to use as bases carbonates and hydrogen carbonates of alkali metals and alkaline-earth metals, such as calcium carbonate, barium carbonate, potassium carbonate, sodium carbonate, sodium hydrogen carbonate and calcium hydrogen carbonate. Further suitable bases are alcoholates derived from the radical R according to the above definition, in particular the corresponding sodium and potassium alcoholates. The use of alcoholates of this kind has the advantage that the corresponding esters are obtained directly, whereas with the use of hydroxides of alkali metals and alkaline-earth metals, there are firstly obtained the salts of these bases with the formed cyclopropanecarboxylic acid. These can however likewise be converted in a simple manner known per se into esters, for example by conversion into the corresponding acid chloride and reaction with an alcohol derived from the radical R. The conversion of a compound of the formula I into a cyclopropanecarboxylic acid derivative of the formula VII is advantageously performed, depending on the type of base used, in an aqueous, aqueous-organic or organic medium. When an alkali metal carbonate or alkaline-earth metal carbonate is used as base, the reaction is performed in an aqueous or aqueous-organic medium. Also the reaction in the presence of hydroxides of alkali metals or of alkaline-earth metals and of hydrogen carbonates of alkali metals is advantageously performed in an aqueous or aqueous-organic medium. There are obtained, after acidification of the reaction mixture, for example by the addition of concentrated hydrochloric acid, the free cyclopropanecarboxylic acids of the formula VII (R=H), which can be optionally converted into the corresponding acid chlorides.

Suitable solvents for the reaction of the cyclobutanones of the formula I to give the cyclopropanecarboxylic acid derivatives of the formula VII in an aqueous-organic or organic medium are lower alcohols, for example those having 1–6 atoms, benzyl alcohol, aliphatic and cyclic ethers, such as diethyl ether, di-n-propyl ether, di-isopropylether, tetrahydrofuran and dioxane, as well as aliphatic, cycloaliphatic or aromatic hydrocarbons, such as n-pentane, n-hexane, cyclohexane, benzene, toluene and xylenes.

The stated reaction is performed in general at the boiling point of the selected reaction medium. Reaction temperatures which are particularly suitable are between about 40° and 120° C.

In the conversion of the cyclobutanones of the formula I into the cyclopropanecarboxylic acid derivatives of the formula VII, there occur as intermediates the corresponding 2-(2',2'-dichloro-3',3',3'-trifluoropropyl)- or 2-(2',2',3'-trichloro-3',3'-difluoropropyl)-cyclopropanecarboxylic acid derivatives of the formula X

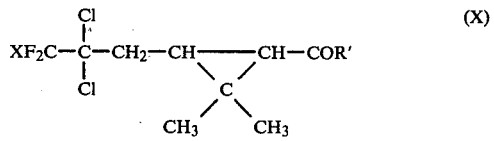

wherein R'=R but has a meaning other than halogen, and X has the given meaning. These intermediates can be isolated if the reaction temperature is held below 40° C. and/or an amount lower than the equivalent amount of a base is used. They convert above 40° C. on addition of a further base, with the splitting-off of HCl, to the corresponding 2-(2'-chloro-3',3',3'-trifluoroprop-1'-en-1'-yl- or 2-(2',3'-dichloro-3',3'-difluoroprop-1'-en-1'-yl)-cyclopropanecarboxylic acid derivatives of the formula VII.

The cyclopropanecarboxylic acid derivatives of the formula X can also be produced photochemically from the cyclobutanones of the formula I by irradiation with UV light, optionally with the addition of customary sensitisers (e.g. ketones, such as acetone, cyclohexanone, benzophenone, acetophenone and higher alkylaryl ketones, thioxanthone, and so forth), in the presence of reagents containing hydroxyl groups, which reagents can simultaneously serve as solvent. Reagents containing hydroxyl groups are for example alkanols, such as methanol and ethanol, and in particular water.

EXAMPLE 1

(a) Production of 2,4,4,5-tetrachloro-5,5-difluoropentane-1-carboxylic acid ethyl ester 204 g of 1,1-difluorotetrachloroethane with 100 g of acrylic acid ethyl ester and 200 ml of acetonitrile as well as 5 g of Cu(I) chloride are heated in an autoclave at 150° C. for 1 hour. The solvent is then distilled off in a water-jet vacuum, and the residue is taken up in 200 ml of diethyl ether. The ether solution is dried with $Na_2SO_4$ and concentrated by evaporation, and the residue is fractionally distilled. The yield is 155 g (51% of theory) of 2,4,4,5-tetrachloro-5,5-difluoropentane-1-carboxylic acid ethyl ester as colourless liquid, which boils at 116°–118° C. and 2000 Pa.

Elementary analysis for $C_7H_8Cl_4F_2O_2$ (molecular weight 303.9):

calculated: C 27.66%, H 2.65%, Cl 46.66%, F 12.50%, found: C 27.9%, H 2.6%, Cl 46.0%, F 12.5%.

IR Spectrum (film): $1760^{-1}$ (CO).

$^1$H-NMR Spectrum ($CDCl_3$) in ppm: 4.66 (X part, J=4 and 8 Hz, CH); 4.26 (q, J=7 Hz, $CH_2$); 3.17 (AB part, J=4 and 8 and 15 Hz, $CH_2$); 1.36 (t, J=7 Hz, $CH_3$).

(b) 2,4,4,5-Tetrachloro-5,5-difluoropentane-1-carboxylic acid 303.9 g of 2,4,4,5-tetrachloro-5,5-difluoropentane-1-carboxylic acid ethyl ester and 900 ml of a 22% aqueous hydrochloric acid are heated at 95°–100° C. for 20 hours. After cooling, the oily suspension obtained is purified, in the customary manner, by means of an ether extraction, bicarbonate extraction and ether extraction of the acidified bicarbonate solution. The yield is 206.9 g (75% of theory of 2,4,4,5-tetrachloro-5,5-difluoropentane-1-carboxylic acid in the form of a clear liquid, which boils at 107°–108° C./25 Pa.

Elementary analysis for $C_5H_4Cl_4F_2O_2$ (mol. weight 275.89):

calculated: C 21.77%, H 1.46%, Cl 51.40%, F 13.77%, found: C 22.0%, H 1.50%, Cl 51.0%, F 13.4%.

IR Spectrum (film): 1740 $cm^{-1}$ (CO).

$^1$H-NMR Spectrum ($CDCl_3/D_2O$) in ppm: 4.75 (X part, J=4 and 7 Hz, $CH_2$); 3.18 (AB part, J=4 and 7 and 15 Hz, CH).

(c) 2,4,4,5-Tetrachloro-5,5-difluoropentane-1-carboxylic acid chloride 276 g of 2,4,4,5-tetrachloro-5,5-difluoropentane-1-carboxylic acid, 300 ml of thionyl chloride and 1 ml of N,N-dimethylformamide are mixed together, and the mixture is heated within 1 hour to 60° C. and finally refluxed for 1 hour. After the excess thionyl chloride has been distilled off, the residue is fractionally distilled to thus obtain 250.2 g (85% of theory) of 2,4,4,5-tetrachloro-5,5-di-fluoropentane-1-carboxylic acid chloride in the form of a clear liquid, which boils at 95°–97° C./2000 Pa.

Elementary analysis for $C_5H_3Cl_5F_2O$ (molecular weight 294.34):

calculated: C 20.40%, H 1.03%, Cl 60.23%, F 12.91%, found: C 20.7%, H 1.1%, Cl 59.8%, F 13.0%.

IR Spectrum (film): 1795 $cm^{-1}$ (CO).

$^1$H-NMR Spectrum ($CDCl_3$) in ppm: 4.97 (X part, J=4 and 8 Hz, CH); 3.23 (AB part, J=4 and 8 and 16 Hz, $CH_2$).

EXAMPLE 2

29.4 g (0.1 mol) of 2,4,4,5-tetrachloro-5,5-difluoropentane-1-carboxylic acid chloride in 350 ml of cyclohexane are placed into an enamel autoclave, whereupon 56 g of isobutylene are injected. Within 4 hours, 10.1 g (0.1 mol) of triethylamine in 100 ml of cyclohexane are pumped in at 65° C., and the reaction mixture is stirred for a further 3 hours at this temperature; it is subsequently filtered until clear and concentrated by evaporation. The residue is chromatographed on silica gel (toluene:hexane 1:1). The yield is 9.9 g of 2-chloro-2-(2',2',2'-trichloro-3',3'-difluoropropyl)-3,3-dimethylcyclobutan-1-one in the form of a colourless oil.

IR Spectrum (film): 1821 $cm^{-1}$ (CO).

$^1$H-NMR Spectrum ($CDCl_3$) in ppm: 3.06 (s, $CH_2$); 3.06 (q, J=16 Hz, $CH_2$); 1.48 and 1.37 (each s, each $CH_3$).

Elementary analysis for $C_9H_{10}Cl_4F_2O$ (molecular weight 313.99):

calculated: C 34.43%, H 3.21%, F 12.10%, Cl 45.17%, found: C 34.4%, H 3.2%, F 12.1%, Cl 45.3%.

EXAMPLE 3

7.1 g of the cyclobutanone produced according to Example 2 are stirred with 0.7 g of tetrabutylammonium chloride at 100°–110° C. for 10 hours, and 50 ml of diethyl ether are then added. The mixture is washed with water, dried over magnesium sulfate and concentrated by evaporation. The residue (6.85 g) is dissolved in toluene/hexane (1:1) and the solution is filtered through a small amount of silica gel. The filtrate is concentrated by evaporation to yield 6.28 g of 4-chloro-3,3-dimethyl-2-(2',2',3'-trichloro-3',3'-difluoropropyl)-cyclobutan-1-one as oil.

$^1$H-NMR Spectrum ($CDCl_3$) in ppm: 4.78 (d, J=2 Hz,H-$C_2$); 3.50 (X part split up with 2 Hz, J=4 and 6 Hz, H-$C_4$); 2.65 (AB part, J=4 and 6 and 15 Hz, $CH_2$); 1.65 and 1.12 (each 1 s, each $CH_3$).

Elementary analysis for $C_9H_{10}Cl_4F_2O$ (molecular weight 313.99):

calculated: C 34.43%, H 3.21%, Cl 45.17%, F 12.10%, found: C 34.5%, H 3.0%, Cl 45.2%, F 11.9%.

EXAMPLE 4

5.9 g of the oil obtained according to Example 3 are stirred with 15 ml of NaOH (10%) overnight at 0°–15° C., and water is then added to the thick suspension formed. The water phase is washed with diethyl ether, acidified with 2 N HCl and extracted with diethyl ether. The extract is dried over magnesium sulfate and concentrated by evaporation, and the residue is digested in n-hexane. The yield is 3.7 g of 2,2-dimethyl-3-(2',2',3'-trichloro-3',3'-difluoropropyl)-cyclopropanecarboxylic acid as a white powder having a melting point of 105°–115° C. The cyclopropanecarboxylic acid consists, according to NMR, of a cis/trans mixture of about 1:1.

IR Spectrum ($CHCl_3$): 1720 $cm^{-1}$.

$^1$H-NMR Spectrum ($CDCl_3/D_2O$) in ppm: 2.28-3.0 (m, $CH_2$); 1.4–2.0 (m, CH-CH); at 1.46 the doublet with J=6 Hz of H-$C_1$ of the trans compound atttached; 1.25 and 1.37 (each 1 s, each $CH_3$ of the trans compound); 1.27 and 1.32 (each 1 s, each $CH_3$ of the cis compound).

Elementary analysis for $C_9H_{11}Cl_3F_2O_2$ (molecular weight 295.54):

calculated: C 36.58%, H 3.75%, F 12.86%, Cl 35.99%, found: C 36.9%, H 3.9%, F 12.6%, Cl 35.9%.

EXAMPLE 5

2.95 g of 2,2-dimethyl-3-(2',2',3'-trichloro-3',3'-difluoropropyl)-cyclopropanecarboxylic acid are introduced into a solution of 0.88 g of NaOH in 20 ml of water; the reaction mixture is heated at 100° C. for 5 hours, and after cooling acidified in the customary manner. The crude product is chromatographed on silica gel (toluene/cyclohexane 1:1) to thus obtain the known (±)-cis/trans-3-(E/Z-2',3'-dichloro-3',3'-difluoroprop-1'-en-1'-yl)-2,2-dimethylcyclopropanecarboxylic acid as oil.

$^1$H-NMR Spectrum (CDCl$_3$/D$_2$O) in ppm: 5.2–7.0 (m, 1H); 1.41–2.4 (m, 2H); 1.23–1.37 (m, 6H).

The above 2,2-dimethyl-3-(2',3'-dichloro-3',3'-difluoroprop-1'-en-1'-yl)-cyclopropanecarboxylic acid can be converted, in the manner described in the German Offenlegungsschrift No. 2,802,962, into insecticidal active substances, for example into the corresponding α-cyano-3-phenoxybenzyl ester.

EXAMPLE 6

187.5 g of 1,1,1-trichlorotrifluoroethane, 100 g of acrylic acid ethyl ester, 200 ml of acetonitrile and 5 g of Cu(I) chloride are heated for 4 hours at 140° C. in an autoclave. The solvent is then distilled off in a water-jet vacuum, and the residue is taken up in 200 ml of diethyl ether. The ether solution is dried with Na$_2$SO$_4$ and concentrated by evaporation, and the residue is fractionally distilled. The yield is 115.0 g (40% of theory) of 2,4,4-trichloro-5,5,5-trifluoropentan-1-carboxylic acid ethyl ester in the form of a colourless liquid, which boils at 90°–92° C./2000 Pa.

Elementary analysis for $C_7H_8Cl_3F_3O_2$ (molecular weight 287.5):

calculated: C 29.25%, H 2.80%, Cl 36.99%, F 19.82%, found: C 29.5%, H 3.0%, Cl 35.3%, F 19.5%.

IR Spectrum (film) 1765 cm$^{-1}$ (CO).

$^1$H-NMR Spectrum (CDCl$_3$) in ppm: 4.65 (X part, J=4 and 8 Hz, CH); 4.28 (q, J=7 Hz, CH$_2$); 3.12 (AB part, J=4 and 8 and 15 Hz, CH$_2$); 1.36 (t, J=7 Hz, CH$_3$).

EXAMPLE 7

The 2,4,4-trichloro-5,5,5-trifluoropentane-1-carboxylic acid ethyl ester obtained according to Example 6 is converted, in the manner described in Examples 2–6, into the known (±)-cis/trans-3-(E/Z/-2'-chloro-3',3',3'-trifluoroprop-1'-en-1'-yl)-2,2-dimethylcyclopropanecarboxylic acid, which in its turn is converted in a known manner into insecticidal active substances of the type described in the German Offenlegungsschrift No. 2,802,962.

What is claimed is:

1. A compound of the formula I

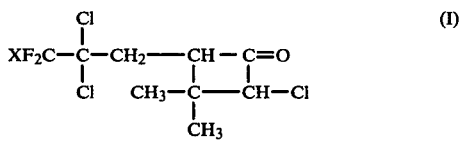

wherein X is chlorine or fluorine.

2. A compound of the formula III

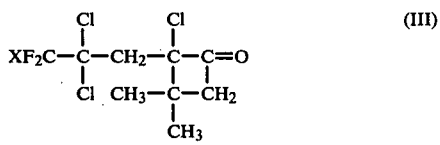

wherein X is chlorine or fluorine.

* * * * *